(12) United States Patent
Campbell

(10) Patent No.: US 12,369,531 B2
(45) Date of Patent: Jul. 29, 2025

(54) AGRICULTURAL BALER SYSTEM WITH A CONTROLLER THAT UPDATES A FIELD MAP BASED ON A MEASURED PARAMETER

(71) Applicant: CNH Industrial America LLC, New Holland, PA (US)

(72) Inventor: Bryce Campbell, Lancaster, PA (US)

(73) Assignee: CNH Industrial America LLC, New Holland, PA (US)

( * ) Notice: Subject to any disclaimer, the term of this patent is extended or adjusted under 35 U.S.C. 154(b) by 1055 days.

(21) Appl. No.: 17/337,199

(22) Filed: Jun. 2, 2021

(65) Prior Publication Data
US 2022/0386535 A1    Dec. 8, 2022

(51) Int. Cl.
*A01F 15/08* (2006.01)
*G01C 21/00* (2006.01)
(Continued)

(52) U.S. Cl.
CPC ...... *A01F 15/0875* (2013.01); *G01C 21/3848* (2020.08); *G01G 19/08* (2013.01);
(Continued)

(58) Field of Classification Search
CPC .................. A01F 15/0875; A01F 15/07; A01F 2015/0891; A01F 15/08; G01C 21/3848;
(Continued)

(56) References Cited

U.S. PATENT DOCUMENTS

| 7,096,653 B2 | 8/2006 | Shinners et al. | |
| 8,994,519 B1 * | 3/2015 | Fuchs | E02F 5/285 340/435 |

(Continued)

FOREIGN PATENT DOCUMENTS

| CN | 108627856 A | 10/2018 | |
| EP | 1095555 A1 * | 5/2001 | ......... A01D 78/1085 |

OTHER PUBLICATIONS

Extended European Search Report for EP Application No. 22175597.8 dated Oct. 31, 2022 (six pages).

*Primary Examiner* — Peter D Nolan
*Assistant Examiner* — Demetra R Smith-Stewart
(74) *Attorney, Agent, or Firm* — Rebecca Henkel; Rickard K. DeMille; Peter K. Zacharias

(57) ABSTRACT

An agricultural baler system includes: an agricultural baler including a bale chamber configured to form a bale from crop material, a crop conveyor configured to feed crop material into the bale chamber, a location sensor configured to output a location signal corresponding to a location of the agricultural baler, and a parameter sensor configured to output a parameter signal corresponding to a measured parameter; and a controller operably coupled to the travel sensor and the parameter sensor. The controller is configured to: determine an area based at least partially on a rake width of a rake and a defined length; determine a parameter distribution in a region of a field having the area based at least partially on the measured parameter and the location of the agricultural baler; and output a field map update signal to update a field map to indicate the determined parameter distribution.

18 Claims, 6 Drawing Sheets

(51) Int. Cl.
  *G01G 19/08* (2006.01)
  *G01N 33/00* (2006.01)
  *G01S 19/01* (2010.01)
  *A01F 15/07* (2006.01)

(52) U.S. Cl.
  CPC .......... *G01N 33/0098* (2013.01); *G01S 19/01* (2013.01); *A01F 15/07* (2013.01); *A01F 2015/0891* (2013.01)

(58) Field of Classification Search
  CPC .... G01G 19/08; G01N 33/0098; G01S 19/01; G05D 1/0219; A01B 69/008
  See application file for complete search history.

(56) References Cited

U.S. PATENT DOCUMENTS

| | | |
|---|---|---|
| 9,253,941 B2 | 2/2016 | Clark |
| 10,036,663 B2 | 7/2018 | Smith |
| 10,289,696 B2 | 5/2019 | Derscheid |
| 2015/0379721 A1 | 12/2015 | Good et al. |
| 2017/0041407 A1* | 2/2017 | Wilbur .................. G06Q 50/02 |
| 2017/0118918 A1 | 5/2017 | Chaney et al. |
| 2017/0318749 A1 | 11/2017 | Kraus et al. |
| 2018/0121467 A1* | 5/2018 | Derscheid ............ G01G 19/414 |
| 2018/0184594 A1 | 7/2018 | Chaney et al. |
| 2018/0281844 A1* | 10/2018 | Wijffels ............... B62D 5/0472 |
| 2018/0303031 A1* | 10/2018 | Araki .................. A01D 43/085 |
| 2019/0289769 A1 | 9/2019 | Antich |
| 2020/0045873 A1 | 2/2020 | Wolters et al. |
| 2020/0167703 A1 | 5/2020 | Tatge et al. |
| 2021/0137015 A1* | 5/2021 | Ibuki .................. A01B 79/005 |

\* cited by examiner

AGRICULTURAL BALER SYSTEM WITH A CONTROLLER THAT UPDATES A FIELD MAP BASED ON A MEASURED PARAMETER

FIELD OF THE INVENTION

The present invention pertains to agricultural vehicles and, more specifically, to agricultural balers and agricultural baler systems for producing crop material bales.

BACKGROUND OF THE INVENTION

Agricultural machines, such as balers, are well-known for collecting cut crop material and packing the cut crop material into bales for easier transport. A typical baler has a crop conveyor, which also may be referred to as a "pickup", that utilizes tines or other elements to direct the cut crop material to a bale chamber that packs the crop material into a bale. After the crop material is packed into a bale with the desired size, the bale is ejected out the back of the baler through a tailgate. While known balers are effective for collecting and packing crop material, such balers may be operated inefficiently for the conditions of the field.

What is needed in the art is a way to improve the efficiency of agricultural balers.

SUMMARY OF THE INVENTION

Exemplary embodiments disclosed herein provide a baler with a controller that is configured to update a field map to indicate a determined parameter distribution.

In some exemplary embodiments provided according to the present disclosure, an agricultural baler system includes an agricultural baler and a controller. The agricultural baler includes: a chassis; a bale chamber carried by the chassis and configured to form a bale from crop material; a crop conveyor configured to feed crop material into the bale chamber; a location sensor carried by the chassis and configured to output a location signal corresponding to a location of the agricultural baler; and a parameter sensor carried by the chassis and configured to output a parameter signal corresponding to a measured parameter. The controller is operably coupled to the location sensor and the parameter sensor. The controller is configured to: determine an area based at least partially on a rake width of a rake and a defined length; determine a parameter distribution in a region of a field having the area based at least partially on the measured parameter and the location of the agricultural baler; and output a field map update signal to update a field map to indicate the determined parameter distribution.

In some embodiments, a method of updating a field map is provided. The method is performed by a controller of an agricultural baler system and includes: receiving a location signal corresponding to a location of an agricultural baler output by a location sensor and a parameter signal corresponding to a measured parameter output by a parameter sensor; determining an area based at least partially on a rake width of a rake and a defined length; determining a parameter distribution in a region of a field having the area based at least partially on the measured parameter and the location of the agricultural baler; and outputting a field map update signal to update the field map to indicate the determined parameter distribution.

One possible advantage that may be realized by exemplary embodiments disclosed herein is the conditions of a field can be indicated on the field map so operating parameters of the baler can be adjusted accordingly.

Another possible advantage that may be realized by exemplary embodiments disclosed herein is that the baler can be used to measure and track useful parameters for a user such as crop material density in the foil and moisture.

BRIEF DESCRIPTION OF THE DRAWINGS

For the purpose of illustration, there are shown in the drawings certain embodiments of the present invention. It should be understood, however, that the invention is not limited to the precise arrangements, dimensions, and instruments shown. Like numerals indicate like elements throughout the drawings. In the drawings.

DETAILED DESCRIPTION OF THE INVENTION

Figure 1:
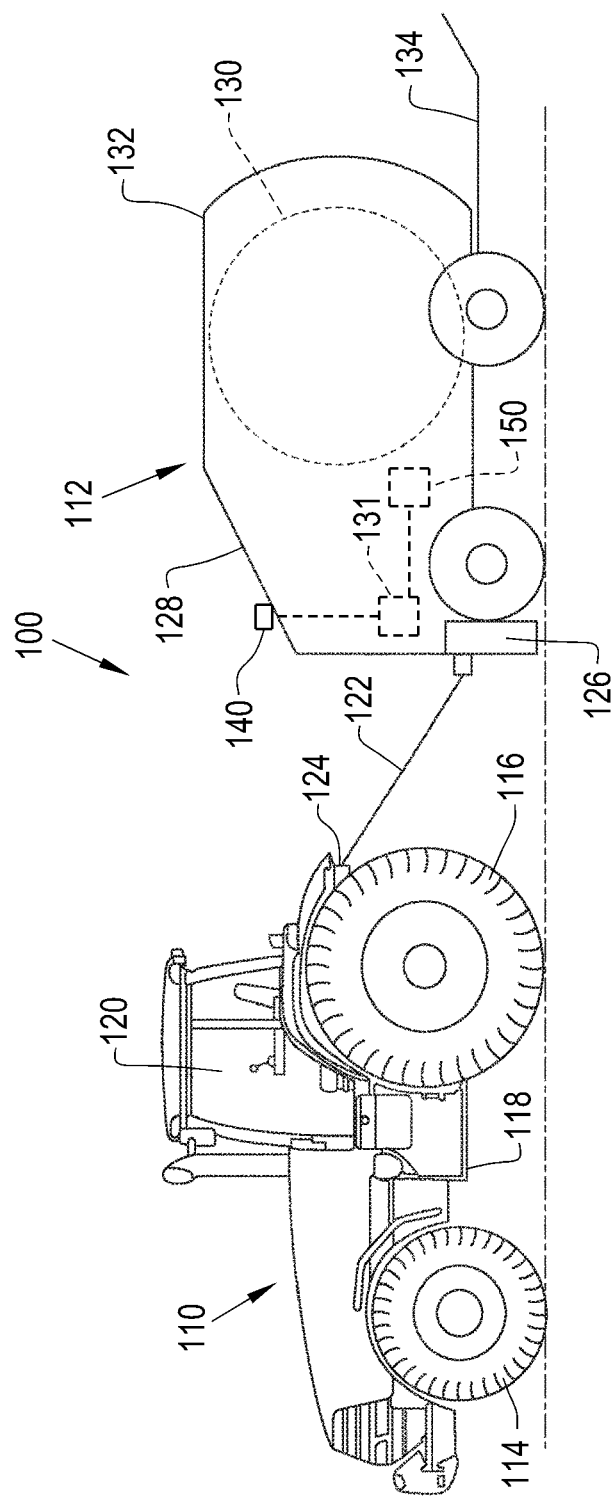
FIG. 1 illustrates a side view of an exemplary embodiment of a tractor and a baler that may be part of an agricultural baler system, provided in accordance with the present disclosure.

Referring now to the drawings, FIG. 1 illustrates a side view of an exemplary embodiment of a work vehicle 110 towing an agricultural baler 112 in accordance with the present disclosure to perform a baling operation within a field. As will be described further herein, the baler 112 may be part of an agricultural baler system 100 for producing crop material bales that includes the baler 112 and, in some embodiments, the work vehicle 110. As shown, the work vehicle 110 is configured as an agricultural tractor, such as an operator-driven tractor or an autonomous tractor. However, in some embodiments, the work vehicle 110 may correspond to any other suitable vehicle configured to tow a baler across a field or that is otherwise configured to facilitate the performance of a baling operation, including an autonomous baling vehicle. Additionally, as shown, the baler 112 is configured as a round baler configured to generate round bales. However, in some embodiments, the baler 112 may have any other suitable configuration, including being configured to generate square or rectangular bales. It should be further appreciated that the baler 112, while shown as being towed by a tractor 110, may also be a self-propelled baler that does not rely on a separate vehicle for propulsion and/or power to function.

As shown in FIG. 1, the work vehicle 110 includes a pair of front wheels 114, a pair of rear wheels 116, and a chassis 118 coupled to and supported by the wheels 114, 116. An operator's cab 120 may be supported by a portion of the chassis 118 and may house various input devices for permitting an operator to control the operation of the work vehicle 110 and/or the baler 112. Additionally, the work vehicle 110 may include an engine and a transmission mounted on the chassis 118. The transmission may be operably coupled to the engine and may provide variably adjusted gear ratios for transferring engine power to the wheels 116 via a drive axle assembly.

As shown in FIG. 1, the work vehicle 110 may be coupled to the baler 112 via a tongue 122 mounted on a hitch 124 of the work vehicle 110 to allow the vehicle 110 to tow the baler 112 across the field. As such, the work vehicle 110 may, for example, guide the baler 112 toward crop material deposited in windrows on the field. As is generally understood, to collect the crop material, the baler 112 includes a chassis 125 that carries a crop conveyor 126 (shown schematically in FIG. 1) mounted on the front end of the baler 112. The crop conveyor 126 may, for example, have a rotating wheel with tines that collects crop material from the ground and feeds the crop material toward a bale chamber 128 of the baler 112. Inside the bale chamber 128, rollers, belts, and/or other devices compact the crop material to form a generally cylindrically shaped bale 130. The bale 130 is contained within the baler 112 until ejection of the bale 130 is instructed (e.g., by the operator and/or a baler controller 131). In some embodiments, the bale 130 may be automatically ejected from the baler 112 once the bale 130 is formed by the baler controller 131 detecting that the bale 130 is fully formed and outputting an appropriate ejection signal.

As shown in FIG. 1, the baler 112 may also include a tailgate 132 movable between a closed position (as shown in the illustrated embodiment) and an opened position via a suitable actuator assembly. The tailgate 132 and/or actuator assembly may be controlled to open and close by the baler controller 131. In the closed position, the tailgate 132 may confine or retain the bale 130 within the baler 112. In the open position, the tailgate 132 may rotate out of the way to allow the bale 130 to be released from the bale chamber 128. Additionally, as shown in FIG. 1, the baler 112 may include a ramp 134 extending from its aft end that is configured to receive and direct the bale 130 away from the baler 112 as it is being released from the bale chamber 128. In some embodiments, the ramp 134 may be spring loaded, such that the ramp 134 is urged into a raised position, as illustrated. In such embodiments, the weight of the bale 130 on the ramp 134 may drive the ramp 134 to a lowered position in which the ramp 134 directs the bale 130 to the soil surface. Once the bale 130 is ejected, the bale 130 may roll down the ramp 134 and be deposited onto the field. As such, the ramp 134 may enable the bale 130 to maintain its shape and desired density by gently guiding the bale 130 onto the field.

It should be appreciated that the configuration of the work vehicle 110 described above and shown in FIG. 1 is provided only as one example. Thus, it should be appreciated that the present disclosure may be readily adaptable to any manner of work vehicle configuration. For example, in an alternative embodiment, a separate frame or chassis may be provided to which the engine, transmission, and drive axle assembly are coupled, a configuration common in smaller tractors. Still other configurations may use an articulated chassis to steer the work vehicle 110, or rely on tracks in lieu of the wheels 114, 116. Additionally, as indicated previously, the work vehicle 110 may, in some embodiments, be configured as an autonomous vehicle. In such embodiments, the work vehicle 110 may include suitable components for providing autonomous vehicle operation and, depending on the vehicle configuration, need not include the operator's cab 120.

Additionally, it should be appreciated that the configuration of the baler 112 described above and shown in FIG. 1 is provided only as one example. Thus, it should be appreciated that the present disclosure may be readily adaptable to any manner of baler configuration. For example, as indicated previously, the baler 112 may, in some embodiments, correspond to a square baler configured to generate square or rectangular bales.

Figure 2:
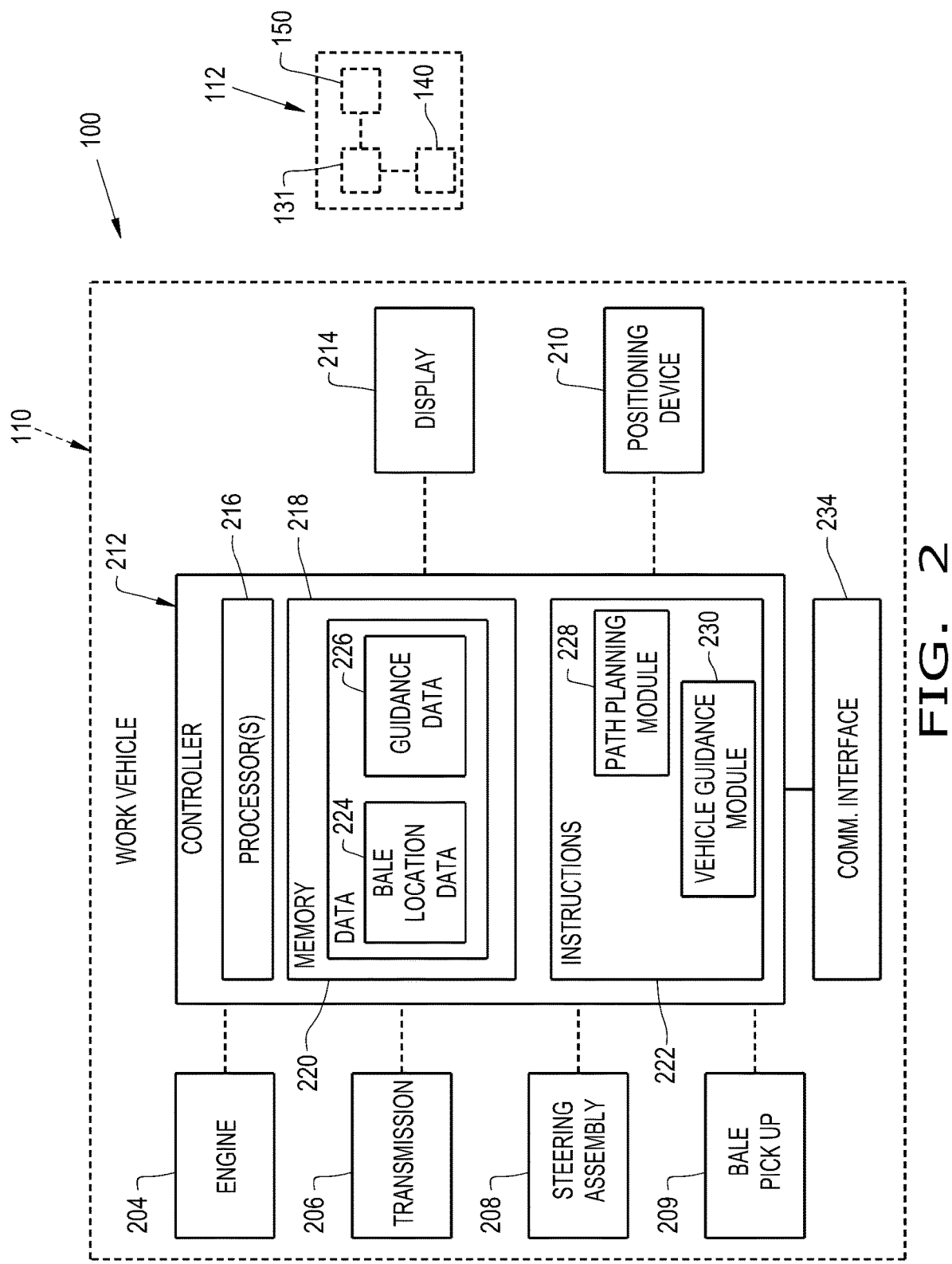
FIG. 2 illustrates a schematic diagram of an exemplary embodiment of the agricultural baler of FIG. 1, provided in accordance with the present disclosure.

Referring now to FIG. 2, a schematic view of an exemplary embodiment of an agricultural baler system 100 for producing crop material bales is illustrated in accordance with the present disclosure. In general, the system 100 will be described herein with reference to the work vehicle 110 and the baler 112 described previously with reference to FIG. 1, as well as a controller as will be described further herein. However, it should be appreciated that the system 100 may generally be utilized with work vehicles having any suitable vehicle configuration and/or balers having any suitable baler configuration.

The system 100 includes the agricultural baler 112 and a controller, which may be the previously described baler controller 131 or, additionally or alternatively, a vehicle vehicle controller 212 of the work vehicle 110. As shown in FIG. 2, the work vehicle 110 may include various components for allowing the work vehicle 110 to be controllably moved across the field during the bale production operation. For example, the work vehicle 110 may include an engine 204 and a transmission 206 coupled to the engine 204 for propelling the work vehicle 110 through the field. In addition, the work vehicle 110 may include a steering assembly 208 for steering the work vehicle 110. In some embodiments, the steering assembly 208 may be configured to be manually operated via the operator to steer the work vehicle 110. The steering assembly 208 may also be configured to be automatically and/or autonomously controlled to allow the work vehicle 110 to be directed along a predetermined path(s) across the field, either additionally or alternatively to manual control of the steering assembly 208. For example, in some embodiments, the steering assembly 208 may include or form part of an auto-guidance system for automatically steering the work vehicle 110. In such an embodiment, the work vehicle 110 may correspond to a fully autonomous vehicle, a semi-autonomous vehicle, or an otherwise manually operated vehicle having one or more autonomous functions (e.g., automated steering or auto-guidance functions).

Additionally, the work vehicle 110 may also include a positioning device 210 configured to monitor or track the position of the work vehicle 110 as it is traversed across a field. For example, in some embodiments, the positioning device 210 may be configured to determine the exact location of the bale retriever 202 using a satellite navigation position system (e.g. a GPS system, a Galileo positioning system, the Global Navigation satellite system (GLONASS), the BeiDou Satellite Navigation and Positioning system, and/or the like).

As shown in FIG. 2, the work vehicle 110 may also include a vehicle controller 212. The vehicle controller 212 is operatively coupled to the steering assembly 208 and, in some embodiments, one or more other components of the work vehicle 110 (e.g., the engine 204 and/or the transmission 206) for electronically controlling the operation of such component(s) (e.g. electronic control based on inputs received from the operator and/or automatic electronic control for executing one or more autonomous control functions). The vehicle controller 212 may be configured to generate one or more paths for the bale production operation. For example, the vehicle controller 212 may be configured to generate guidance lines for collecting windrows deposited within the field. The vehicle controller 212 may then utilize the guidance lines for guiding the work vehicle 110 and the baler 112 across the field so the baler 112 collects crop material of the windrows and forms bales from the gathered crop material. For example, in some embodiments, the vehicle controller 212 may be configured to automatically control the operation of the baler 112 via control of the steering assembly 208 such that the baler 112 is moved across the field along the determined guidance lines without any operator input (e.g., for autonomous vehicle operation and/or when otherwise operating in an autonomous mode). Alternatively, the vehicle controller 212 may be configured to display the determined guidance lines on an associated display 214 to allow the operator to navigate the work vehicle 110 across the field based on the displayed guidance lines.

In general, the vehicle controller 212 may correspond to any suitable processor-based device(s), such as a computing device or any combination of computing devices. Thus, as shown in FIG. 2, the vehicle controller 212 may generally include one or more processor(s) 216 and associated memory 218 configured to perform a variety of computer-implemented functions (e.g., performing the methods, steps, algorithms, calculations and the like disclosed herein). As used herein, the term "processor" refers not only to integrated circuits referred to in the art as being included in a computer, but also refers to a controller, a microcontroller, a microcomputer, a programmable logic controller (PLC), an application specific integrated circuit, and other programmable circuits. Additionally, the memory 218 may generally comprise memory element(s) including, but not limited to, computer readable medium (e.g., random access memory (RAM)), computer readable non-volatile medium (e.g., a flash memory), a floppy disk, a compact disc-read only memory (CD-ROM), a magneto-optical disk (MOD), a digital versatile disc (DVD) and/or other suitable memory elements. Such memory 218 may generally be configured to store information accessible to the processor(s) 216, including data 220 that can be retrieved, manipulated, created and/or stored by the processor(s) 216 and instructions 222 that can be executed by the processor(s) 216.

In some embodiments, the data 220 may be stored in one or more databases. For example, the memory 218 may include a bale location database 224 for storing data associated with the bales to be collected from the field during the performance of the baling operation. Such data may, for instance, include any data collected during the performance of the baling operation, such as the position data associated with the location of the baling paths relative to the field, the heading data associated with the heading of the vehicle/baler along each baling path, and/or the position data associated with the specific location of each bale within the field. In addition, various other types of data may be stored within the bale location database 224. For example, in some embodiments, data may be stored within the bale location database 224 that is associated with one or more operator inputs, one or more user-defined system preferences, and/or other system inputs relevant to one or more aspects of the present disclosure, such as data associated with the specific type of bales being collected (e.g., round bales vs. square/rectangular bales), data associated with the specific size of bales being collected (e.g., 4×5, 5×5, or 6×5), data associated with a desired or selected location for the staging area at which the bales will be aggregated, data associated with a desired spacing or arrangement of the collected bales within the staging area, and/or any other relevant data.

Additionally, as shown in FIG. 2, the memory 218 may also include a guidance database 226 for storing data associated with guiding the work vehicle 110 during the performance of the baling operation. For example, as indicated previously, the vehicle controller 212 may be configured to generate guidance lines along which the work vehicle 110 is to be traversed when producing the bales. As such, the guidance database 226 may, for example, include data associated with the computer-generated guidance lines, such as GPS data or map data that maps each guidance line across the field.

Referring still to FIG. 2, in some embodiments, the instructions 222 stored within the memory 218 of the vehicle controller 212 may be executed by the processor(s) 216 to implement a path planning module 228, which may be configured to plan a travel path of the work vehicle 110, and a vehicle guidance module 230, which may be configured to guide the work vehicle 110.

In known agricultural baler systems, a baler is often pulled by a work vehicle, such as a tractor, along a path. However, the baler does not collect, store, and/or analyze parameters that may be useful to an operator, such as crop density, moisture, etc. Thus, the operator may not be operating the baler efficiently and/or may not have any data to use for other operations, such as fertilizing and/or watering the field.

To address some of the issues with known baler systems, and referring still to FIGS. 1-2, the agricultural baler system 100 provided according to the present disclosure includes a location sensor 140 and a parameter sensor 150 carried by the chassis 125 of the baler 112. The location sensor 140, which in some embodiments is also carried by the chassis 125 of the baler 112, is configured to output a location signal corresponding to a location of the baler 112. It should be appreciated that, alternatively or in addition, the location sensor may comprise the positioning device 210 of the work vehicle 110, which can also be used to determine the location of the baler 112 based on the spatial relationship between the baler 112 and the work vehicle 110. The parameter sensor 150 is configured to output a parameter signal corresponding to a measured parameter. Both the location sensor 140 and the parameter sensor 150 are operably coupled to a controller, which may be the baler controller 131 and/or the vehicle controller 212 of the work vehicle 110. In some embodiments, the baler controller 131 and the vehicle controller 212 are part of a controller system that includes the controllers 131, 212 operably coupled together, and in some embodiments one or more additional controllers. For convenience of description, reference to "the controller" further herein is with reference to the vehicle controller 212, but it should be appreciated that the controller described further herein may alternatively be the baler controller 131, a controller system including the baler controller 131 and/or the vehicle controller 212, or another controller.

Figure 3:
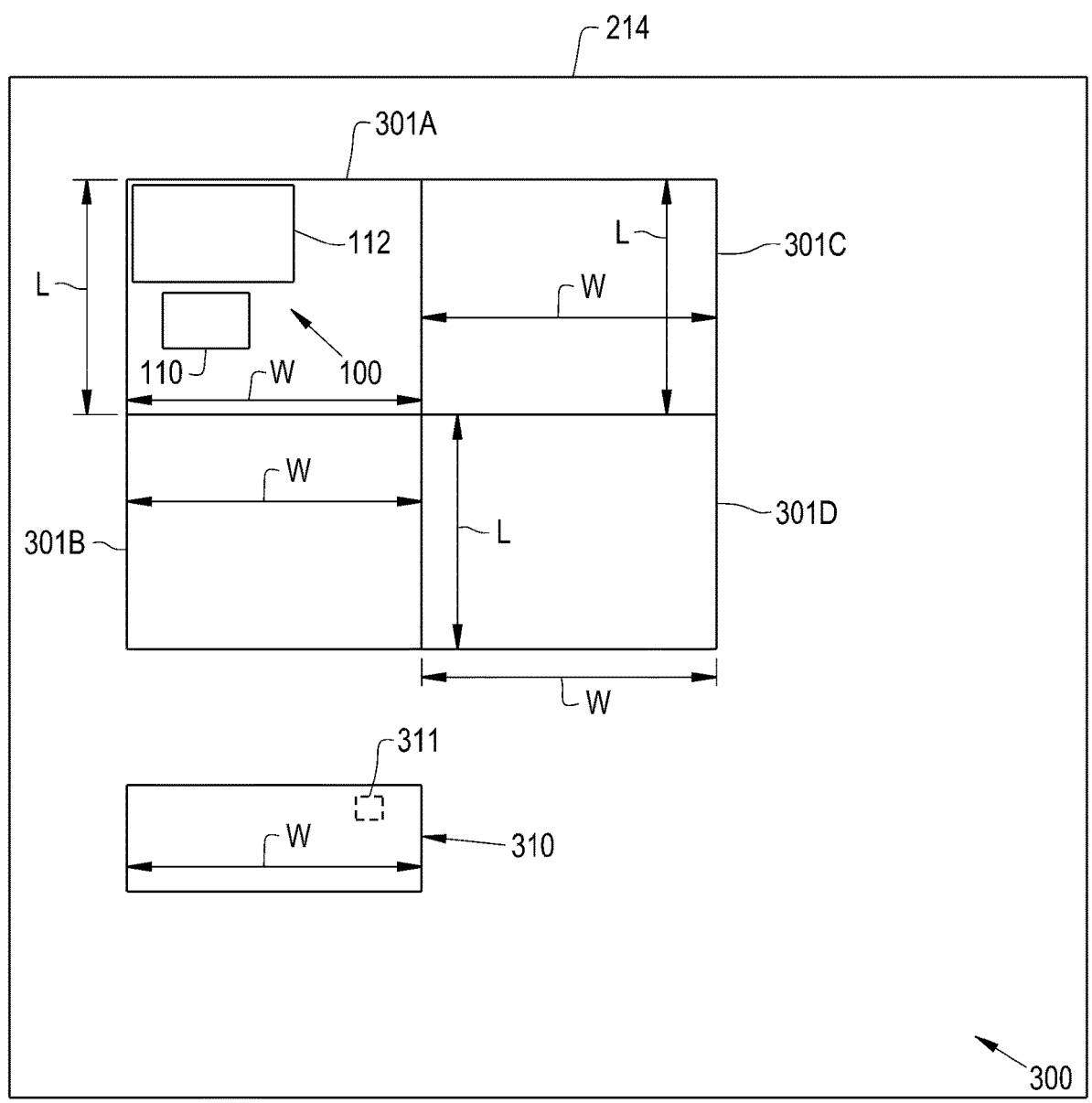
FIG. 3 illustrates an exemplary embodiment of a display presenting a field map that may be updated according to the present disclosure.
Figure 4:
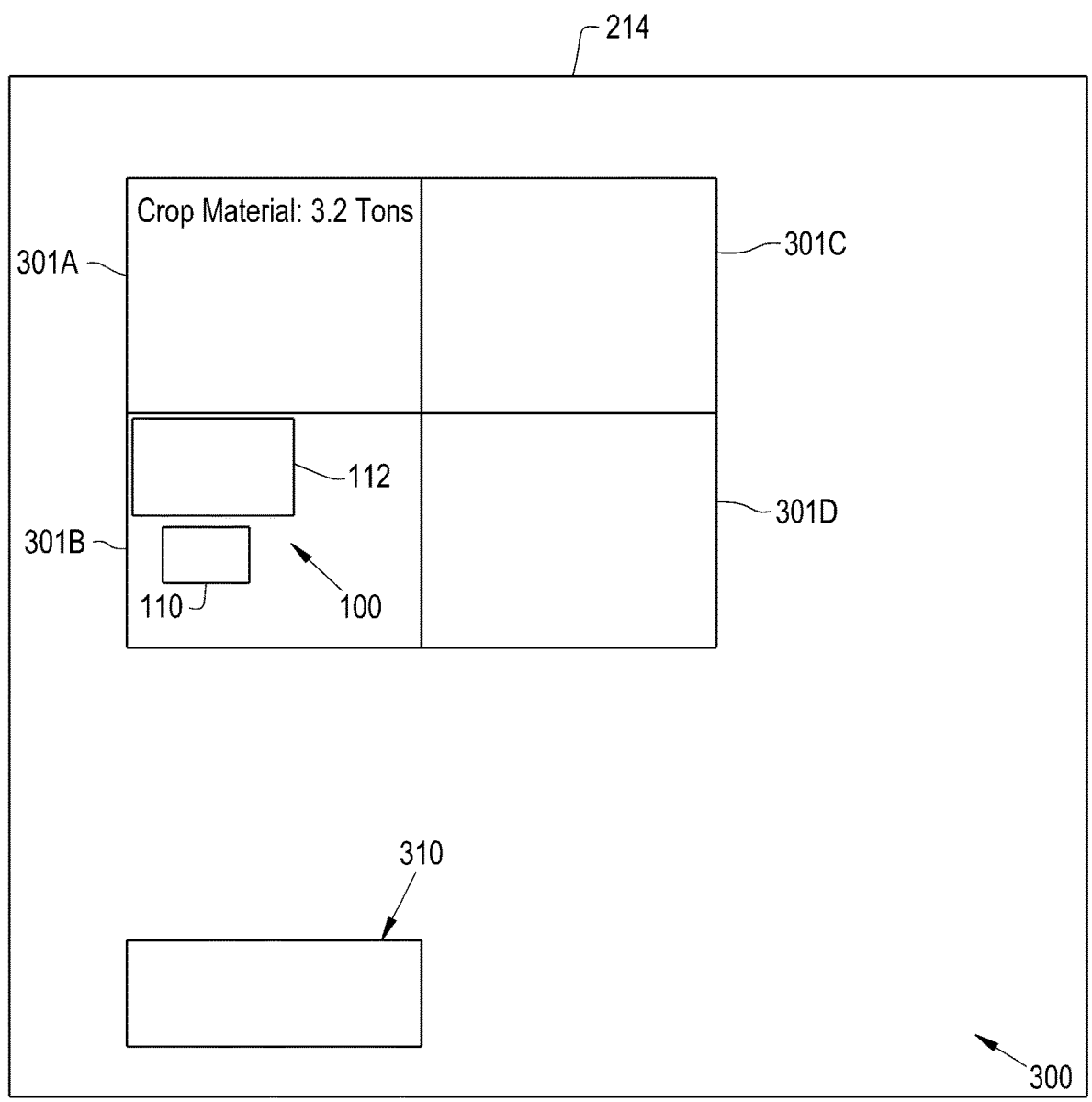
FIG. 4 illustrates the display of FIG. 3 after the field map is updated with a determined parameter distribution.
Figure 5:
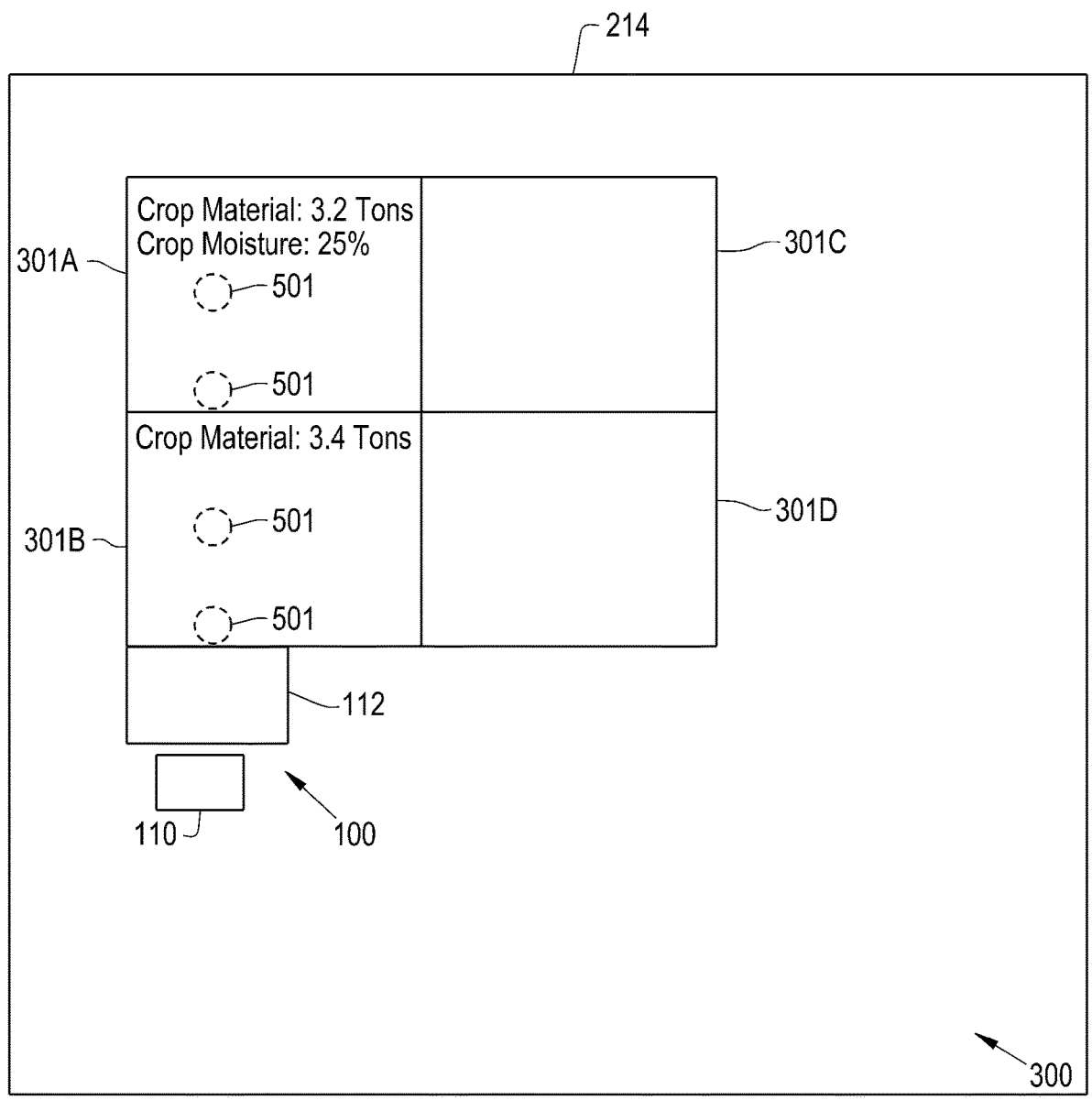
FIG. 5 illustrates the display of FIG. 3 after the field map is updated with a different determined parameter distribution.

Referring now to FIGS. 3-5, exemplary operation of the controller 212 according to the present disclosure is illustrated. FIGS. 3-5 illustrate the display 214 presenting a field map 300, which may be stored in the memory 220. It should be appreciated that while the field map 300 is illustrated in a graphical form in FIGS. 3-5, in some embodiments the field map 300 is stored in the memory 220 without being presented in graphical form, e.g., in a fully autonomous vehicle where a graphical form of the field map 300 for use by an operator is unnecessary.

The controller 212 is configured to determine an area based at least partially on a rake width of a rake and a defined length, determine a parameter distribution in a region of a field having the area based at least partially on the measured parameter and the location of the baler 112, and output a field map update signal to update the field map 300 to indicate the determined parameter distribution. In this respect, the controller 212 can update the field map 300 to indicate how certain parameters are distributed across the field of the field map 300, which may then be used to determine how to operate the baler system 100 and/or support other operations in the field.

As illustrated in FIG. 3, some of the field map 300 may be sub-divided by the controller 212 into a plurality of regions 301A, 301B, 301C, 301D that each define the same area. The area of each region 301A, 301B, 301C, 301D may be defined by the product of a rake width W of a rake 310, which may be used to create windrows in the field of the field map 300, and a defined length L, which may be input by an operator or otherwise defined. The rake width W of the rake 310 corresponds to a working width of the rake 310. In some embodiments, the area of each region 301A, 301B, 301C, 301D may be at least partially based on a whole-number multiple of the rake width W, e.g., two rake widths W, three rake widths W, etc., which may be equal to a number of passes of the rake 310 that make up a windrow in the field, e.g., if the rake 310 takes two passes to form a windrow, the area may be equal to two rake widths W multiplied by the defined length L (2 W*L). In some embodiments, the rake 310 has a communication interface 311 that is configured to output a rake width signal corresponding to the rake width W to a communication interface 234 of the work vehicle 110, which is operably coupled to the controller 212, so the rake width W is automatically known by the controller 212. In some embodiments, an operator may input the rake width W into the display 214, which is configured to output the rake width signal to the controller 212. Similarly, the defined length L may be a defined length that is stored in the memory 220 from a manufacturer's setting, may be transmitted to the controller 212 via the communication interface 234, and/or may be transmitted to the controller 212 via the display 214. It should be appreciated that while the rake 310 is illustrated as being separate from the baler 112, in some embodiments the rake 310 is a part of or otherwise coupled to the baler 112.

To determine the parameter distribution in one of the regions 301A, 301B, 301C, 301D, such as the region 301A, the controller 212 may receive parameter signals from the parameter sensor 150 as the baler 112 travels through the region 301A, based off location signals from the location sensor 140. The measured parameter may be, for example, a weight of crop material gathered by the baler 112 so the parameter sensor 150 is a weight sensor that is configured to output a parameter signal corresponding to a weight, such as a weight of crop material gathered by the baler 112. As the baler 112 travels in the region 301A, the controller 212 may receive multiple parameter signals corresponding to the weight of crop material gathered by the baler 112 to determine how much crop material was gathered by the baler 112 in the region 301A.

In some embodiments, the controller 212 is configured to determine a weight change of the baler 112 from a plurality of parameter signals from the parameter (weight) sensor 150. The controller 212 may, for example, receive a first weight signal corresponding to a starting weight of the baler 112 when the baler 112 first enters the region 301A, as illustrated in FIG. 3, and receive a second weight signal corresponding to an ending weight of the baler 112 when the baler 112 exits the region 301A and travels into an adjacent region, such as region 301B as illustrated in FIG. 4. Based on the starting weight and the ending weight of the baler 112 in the region 301A, the controller 212 can determine the weight change of the baler 112, which can closely correspond to the weight of crop material gathered, by subtracting the starting weight from the ending weight.

The controller 212 may determine the parameter (weight of gathered crop material) distribution in the region 301A by determining the weight of crop material gathered, based on the parameter signal, while the baler 112 is in the region 301A, which the controller 212 can determine based on the location signals from the location sensor 140. For example, if the controller 212 determines that the weight of crop material gathered as the baler 112 travels through the region 301A is 3.2 tons, the controller 212 can determine the parameter distribution in the region 301A to be 3.2 tons of crop material. The controller 212 may then output a field map update signal, to the memory 220 and/or the display 214, to update the field map 300 so the field map 300 indicates the determined parameter distribution, as illustrated in FIG. 4 by the field map 300 indicating that the region 301A has 3.2 tons of crop material. The controller 212 may then perform the same determinations as the baler 112 travels through the region 301B to determine the parameter distribution in the region 301B and output a field map update signal to update the field map 300 to indicate the determined parameter distribution in the region 301B, as illustrated in FIG. 5. While the field map 300 is illustrated as indicating the parameter distribution using alphanumeric characters, the parameter distribution may be indicated in different ways, e.g., by using a color scale. In this respect, the controller 212 can continuously update the field map 300 to indicate one or more parameter distributions in the field and provide data that may be used to efficiently operate the agricultural baler system 100 and/or other systems used in the field. The controller 212 may, for example, be configured to output the field map update signal to the memory 220 to update the field map 300 stored on the memory 220.

While the measured parameter is previously described as being the weight of crop material gathered by the baler 112, it should be appreciated that the measured parameter can be a variety of different parameters. For example, the parameter sensor 150 in the form of a weight sensor may be used to measure a weight of bales that are released from the baler 112. The controller 212 may, for example, output a release signal to the tailgate 132 to cause the tailgate to open and release a bale. The output release signal may also be output to the parameter (weight) sensor 150 to cause the parameter sensor 150 to output a parameter signal to the controller 212 that corresponds to a pre-release weight of the baler 112, which includes the weight of the bale. After the bale is released, the controller 212 may cause the parameter sensor 150 to output another parameter signal to the controller 212 that corresponds to a post-release weight of the baler 112, which no longer includes the weight of the bale due to the release. The controller 212 may then subtract the post-release weight of the baler 112 from the pre-release weight of the baler 112 to determine a weight of the released bale, which the controller 212 can then use to determine the parameter distribution in a region 301A, 301B, 301C, 301D and output the field update signal to update the field map 300 to indicate the determined parameter distribution (the weight of one or more bales released in a region 301A, 301B, 301C, 301D). It should thus be appreciated that the controller 212 can determine the parameter distribution of a variety of parameters related to weight and cause the field map 300 to be updated accordingly. It should be further appreciated that, in some embodiments, the baler 112 may include multiple parameter sensors 150 that each output a respective parameter signal corresponding to a respective measured parameter and the controller 212 is configured to determine a parameter distribution of some or all of the parameters and output the field map update signal to update the field map 300 to indicate the determined parameter distribution of the parameters.

In some embodiments, the controller 212 is configured to determine when a bale is released by the tailgate 132, determine a location of the released bale on the field map 300, and output a bale location signal to update the field map 300 to indicate the determined location of the released bale, indicated as 501 in FIG. 5. The controller 212 may, for example, determine when the bale is released when the controller 212 controls the tailgate 132 to open and determine the location of the released bale 501 on the field map 300 based on the location of the baler 112 when the tailgate 132 opens. In this respect, the controller 212 may be configured to not only update the field map 300 to indicate the parameter distribution in regions 301A, 301B, 301C, 301D of the field, but also to indicate where bales 501 are released in the field map 300 for a bale collector to collect.

In some embodiments, the parameter sensor 150 is a moisture sensor and the measured parameter is a crop material moisture. The crop material moisture may be measured in the bale chamber 128, to measure the instantaneous moisture of crop material being collected. The controller 212 can determine the crop material moisture distribution in a region 301A, 301B, 301C, 301D of the field and output the field map update signal to update the field map 300 to indicate the determined crop material moisture distribution in, for example, the region 301A, as illustrated in FIG. 5. While the crop material moisture distribution is illustrated in FIG. 5 as being indicated by a numeric value, in some embodiments the crop material moisture distribution is indicated by differing colors in the field map 300, i.e., as a color map. The color map may be indicated for an entirety of each of the regions 301A, 301B, 301C, 301D or, for larger regions, the color map may differ within the regions 301A, 301B, 301C, 301D if there are multiple crop material moisture distributions within one or more of the regions 301A, 301B, 301C, 301D. In some embodiments, the controller 212 is configured to receive multiple parameter (crop material moisture) signals corresponding to the crop material moisture of crop material gathered by the baler 112 and to determine an average crop material moisture. The controller 212 may be further configured to determine if one or more crop material moisture readings deviate excessively from other readings, indicating that a part of a field may not have been watered, and output a warning signal to indicate that such a reading occurred. Other measured parameters can include, but are not limited to, the number of bales formed from crop material in a region 301A, 301B, 301C, 301D, the average weight of released bales, and a baling pressure of the bale chamber 128. It should thus be appreciated that the agricultural baler system 100 provided according to the present disclosure can be used to determine parameter distributions other than those related to weight to update a field map 300.

It should be appreciated that, in some embodiments, the baler 112 takes multiple passes through each of the regions 301A, 301B, 301C, 301D during a baling operation. Thus, in some embodiments the controller 212 is configured to store multiple instances of a measured parameter in the memory 220 and determine a parameter distribution in a region 301A, 301B, 301C, 301D of the field based at least partially on one or more stored parameter measurements.

For example, the controller 212 may be configured to store a plurality of parameter measurements, e.g., a weight of crop material gathered by the baler 112, in the memory 220 and determine the parameter (weight of crop material gathered) distribution based on a sum of the stored parameter measurements, giving an accurate indication of the parameter distribution. Alternatively, the controller 212 may be configured to determine the parameter distribution based on the measured parameter and an algorithm that is used to estimate the parameter distribution in the region 301A, 301B, 301C, 301D, i.e., the controller 212 does not need to determine the parameter distribution directly from the measured parameter. It should thus be appreciated that the controller 212 can be configured in a variety of ways to determine the parameter distribution according to the present disclosure.

In some embodiments, the controller 212 is configured to convert the parameter distribution in the regions 301A, 301B, 301C, 301D into standardized units for indication on the field map 300. For example, if the area of each of the regions 301A, 301B, 301C, 301D is equal to one quarter of an acre, the controller 212 may be configured to convert the determined parameter distribution, such as crop material gathered by the baler 112 per quarter acre, into standard measurement units such as crop material gathered by the baler 112 per acre; in such an instance, the controller 212 can be configured to make the conversion by multiplying the determined parameter distribution by 4. It should thus be appreciated that while the controller 212 may be configured to determine the parameter distribution in a region 301A, 301B, 301C, 301D of the field each having an area (based on the wake width W and the defined length L) that is not a standard measurement unit, the controller 212 can convert the determined parameter distribution to a standard measurement unit.

From the foregoing, it should be appreciated that the agricultural baler system 100 provided according to the present disclosure can update a field map 300 based on measured parameters in the field and provide additional data for an operator to utilize for operational decisions. By determining the parameter distribution based at least partially on an area that is based on a rake width W and a defined length L, the determined area can generally correspond to the area of the field that is raked by the rake 310 to form windrows for baling. The defined length L, on the other hand, can be defined and/or adjusted to correspond to differing resolutions of the field map 300, allowing an operator to get as detailed of a field map 300 as desired. Thus, the agricultural baler system 100 provided according to the present disclosure provides a field map 300 that indicates useful information for improving efficiency of various field management operations.

Figure 6:
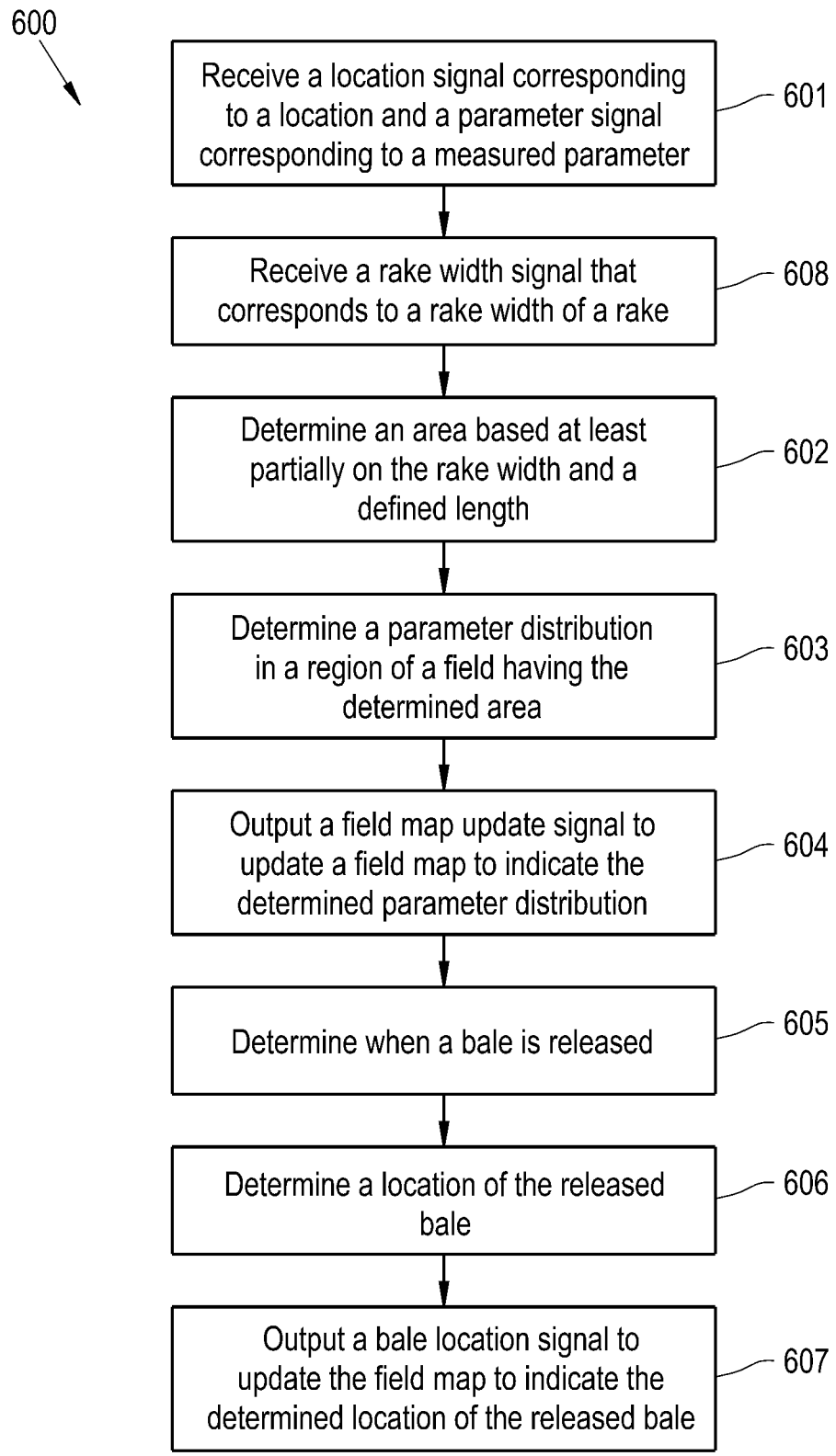
FIG. 6 is a flow chart illustrating an exemplary embodiment of a method of updating a field map, provided in accordance with the present disclosure.

Referring now to FIG. 6, an exemplary embodiment of a method 600 of updating the field map 300 provided according to the present disclosure is illustrated. The method 600 is performed by a controller of the agricultural baler system 100, which may be the vehicle controller 212 and/or the baler controller 131 as previously described. The method 600 includes receiving 601 the location signal corresponding to the location of the agricultural baler 112 output by the location sensor 140 and the parameter signal corresponding to the measured parameter output by the parameter sensor 150; determining 602 the area based at least partially on the rake width W of the rake 310 and the defined length L; determining 603 the parameter distribution in the region 301A, 301B, 301C, 301D of a field having the area based at least partially on the measured parameter and the location of the agricultural baler 112; and outputting 604 the field map update signal to update the field map 300 to indicate the determined parameter distribution. The method 600 may further include determining 605 when a bale is released by the tailgate 132; determining 606 the location of the released bale 501 on the field map 300; and outputting 607 a bale location signal to update the field map 300 to indicate the determined location of the released bale 501. The method 600 may further include receiving 608 the rake width signal from the display 214 or the rake 310 that corresponds to the rake width W of the rake 310. The method 600 may further include any of the previously described functionality of the controller of the agricultural baler system 100.

It is to be understood that the steps of the method 600 are performed by the controller 131, 212 upon loading and executing software code or instructions which are tangibly stored on a tangible computer readable medium, such as on a magnetic medium, e.g., a computer hard drive, an optical medium, e.g., an optical disc, solid-state memory, e.g., flash memory, or other storage media known in the art. Thus, any of the functionality performed by the controller 131, 212 described herein, such as the method 600, is implemented in software code or instructions which are tangibly stored on a tangible computer readable medium. The controller 131, 212 loads the software code or instructions via a direct interface with the computer readable medium or via a wired and/or wireless network. Upon loading and executing such software code or instructions by the controller 131, 212, the controller 131, 212 may perform any of the functionality of the controller 131, 212 described herein, including any steps of the method 600 described herein.

The term "software code" or "code" used herein refers to any instructions or set of instructions that influence the operation of a computer or controller. They may exist in a computer-executable form, such as machine code, which is the set of instructions and data directly executed by a computer's central processing unit or by a controller, a human-understandable form, such as source code, which may be compiled in order to be executed by a computer's central processing unit or by a controller, or an intermediate form, such as object code, which is produced by a compiler. As used herein, the term "software code" or "code" also includes any human-understandable computer instructions or set of instructions, e.g., a script, that may be executed on the fly with the aid of an interpreter executed by a computer's central processing unit or by a controller.

These and other advantages of the present invention will be apparent to those skilled in the art from the foregoing specification. Accordingly, it is to be recognized by those skilled in the art that changes or modifications may be made to the above-described embodiments without departing from the broad inventive concepts of the invention. It is to be understood that this invention is not limited to the particular embodiments described herein, but is intended to include all changes and modifications that are within the scope and spirit of the invention.

The invention claimed is:

1. An agricultural baler system, comprising:
a rake having a rake communication interface, the rake configured to output a rake width signal corresponding to a rake width of the rake via the rake communication interface;
an agricultural baler, comprising:
a chassis;
a bale chamber carried by the chassis and configured to form a bale from crop material;
a crop conveyor configured to feed crop material into the bale chamber;
a location sensor carried by the chassis and configured to output a location signal corresponding to a location of the agricultural baler; and
a parameter sensor carried by the chassis and configured to output a parameter signal corresponding to a measured parameter;
a communication interface; and
a controller operably coupled to the communication interface, the location sensor, and the parameter sensor, the controller being configured to:
receive, from the rake communication interface through the communication interface, the rake width signal;
determine an area based at least partially on the rake width for the rake and a defined length;
determine a parameter distribution in a region of a field having the area based at least partially on the measured parameter and the location of the agricultural baler; and
output a field map update signal to update a field map to indicate the determined parameter distribution.

2. The agricultural baler system of claim 1, wherein the parameter sensor is a weight sensor and the output parameter signal corresponds to a weight.

3. The agricultural baler system of claim 2, wherein the output parameter signal corresponds to a weight of crop material gathered by the agricultural baler.

4. The agricultural baler system of claim 3, wherein the controller is configured to determine a weight change of the agricultural baler based on a plurality of parameter signals from the weight sensor to determine the weight of crop material gathered by the agricultural baler.

5. The agricultural baler system of claim 2, wherein the agricultural baler further comprises a tailgate configured to open and release a bale, wherein the measured parameter corresponds to a weight of a released bale.

6. The agricultural baler system of claim 5, wherein the controller is configured to determine when a bale is released by the tailgate, determine a location of the released bale on the field map, and output a bale location signal to update the field map to indicate the determined location of the released bale.

7. The agricultural baler system of claim 1, further comprising a memory operably coupled to the controller, the memory being configured to store the field map, the controller being configured to output the field map update signal to the memory to update the field map stored on the memory.

8. The agricultural baler system of claim 1, further comprising a display operably coupled to the controller and configured to display the field map.

9. The agricultural baler system of claim 1, wherein the parameter sensor is a moisture sensor and the measured parameter is a crop material moisture.

10. A method of updating a field map, the method being performed by a controller of an agricultural baler system and comprising:
receiving a rake width signal for a rake from a rake communication interface of the rake, the rake width signal corresponding to a rake width of the rake;
receiving a location signal corresponding to a location of an agricultural baler output by a location sensor and a parameter signal corresponding to a measured parameter output by a parameter sensor;
determining an area based at least partially on the rake width of the rake and a defined length;

determining a parameter distribution in a region of a field having the area based at least partially on the measured parameter and the location of the agricultural baler; and outputting a field map update signal to update the field map to indicate the determined parameter distribution.

11. The method of claim 10, wherein the parameter sensor is a weight sensor and the output parameter signal corresponds to a weight.

12. The method of claim 11, wherein the output parameter signal corresponds to a weight of crop material gathered by the agricultural baler.

13. The method of claim 12, wherein the weight of crop material gathered by the agricultural baler is determined by determining a weight change of the agricultural baler based on a plurality of parameter signals from the weight sensor.

14. The method of claim 11, wherein the agricultural baler comprises a tailgate configured to open and release a bale, wherein the measured parameter corresponds to a weight of a released bale.

15. The method of claim 14, further comprising:
determining when a bale is released by the tailgate;
determining a location of the released bale on the field map; and
outputting a bale location signal to update the field map to indicate the determined location of the released bale.

16. The method of claim 10, wherein the agricultural baler system comprises a memory operably coupled to the controller, the memory being configured to store the field map, wherein the outputting comprises outputting the field map update signal to the memory to update the field map stored on the memory.

17. The method of claim 10, wherein the agricultural baler comprises a display operably coupled to the controller and configured to display the field map.

18. The method of claim 10, wherein the parameter sensor is a moisture sensor and the measured parameter is a crop material moisture.

* * * * *